(12) United States Patent
Brammer et al.

(10) Patent No.: US 8,741,173 B2
(45) Date of Patent: Jun. 3, 2014

(54) HYDROFORMYLATION PROCESS

(75) Inventors: Michael A. Brammer, Lake Jackson, TX (US); Richard W. Wegman, South Charleston, WV (US)

(73) Assignee: Dow Technology Investments LLC

( * ) Notice: Subject to any disclaimer, the term of this patent is extended or adjusted under 35 U.S.C. 154(b) by 0 days.

(21) Appl. No.: 13/877,386

(22) PCT Filed: Sep. 21, 2011

(86) PCT No.: PCT/US2011/052500
§ 371 (c)(1),
(2), (4) Date: Apr. 2, 2013

(87) PCT Pub. No.: WO2012/047514
PCT Pub. Date: Apr. 12, 2012

(65) Prior Publication Data
US 2013/0204024 A1    Aug. 8, 2013

Related U.S. Application Data

(60) Provisional application No. 61/389,972, filed on Oct. 5, 2010.

(51) Int. Cl.
*C09K 3/00* (2006.01)
*C07F 9/02* (2006.01)
*C07C 45/00* (2006.01)
*B01J 31/00* (2006.01)

(52) U.S. Cl.
USPC .......... 252/182.12; 568/17; 568/454; 556/21; 502/167

(58) Field of Classification Search
USPC .................. 556/21; 568/17, 454; 252/182.12; 502/167
See application file for complete search history.

(56) References Cited

U.S. PATENT DOCUMENTS

| | | | |
|---|---|---|---|
| 3,415,906 A | 12/1968 | Shepard et al. | |
| 3,527,809 A | 9/1970 | Pruett et al. | |
| 4,148,830 A | 4/1979 | Pruett et al. | |
| 4,169,861 A | 10/1979 | Hughes | |
| 4,215,077 A | 7/1980 | Matsumoto et al. | |
| 4,247,486 A | 1/1981 | Brewester et al. | |
| 4,491,675 A | 1/1985 | Abatjoglou et al. | |
| 4,518,809 A | 5/1985 | Forster et al. | |
| 4,528,403 A | 7/1985 | Tano et al. | |
| 4,567,302 A | 1/1986 | Sivaramakrishnan | |
| 4,567,306 A | 1/1986 | Dennis et al. | |
| 4,593,011 A | 6/1986 | Abatjoglou et al. | |
| 4,593,127 A | 6/1986 | Bunning et al. | |
| 4,599,206 A | 7/1986 | Billig et al. | |
| 4,668,651 A | 5/1987 | Billig et al. | |
| 4,717,775 A | 1/1988 | Billig et al. | |
| 4,748,261 A | 5/1988 | Billig et al. | |
| 4,769,498 A | 9/1988 | Billig et al. | |
| 4,774,361 A | 9/1988 | Maher et al. | |
| 4,835,299 A | 5/1989 | Maher et al. | |
| 4,885,401 A | 12/1989 | Billig et al. | |
| 4,969,953 A | 11/1990 | Miyazawa et al. | |
| 5,059,710 A | 10/1991 | Abatjoglou et al. | |
| 5,102,505 A | 4/1992 | Sorensen | |
| 5,110,990 A | 5/1992 | Blessing et al. | |
| 5,113,022 A | 5/1992 | Abatjoglou et al. | |
| 5,114,473 A | 5/1992 | Abatjoglou et al. | |
| 5,179,055 A | 1/1993 | Wink et al. | |
| 5,202,297 A | 4/1993 | Lorz et al. | |
| 5,233,093 A | 8/1993 | Pitchai et al. | |
| 5,235,113 A | 8/1993 | Sato et al. | |
| 5,254,741 A | 10/1993 | Lorz et al. | |
| 5,264,616 A | 11/1993 | Roeper et al. | |
| 5,288,918 A | 2/1994 | Maher et al. | |
| 5,312,996 A | 5/1994 | Packett | |
| 5,364,950 A | 11/1994 | Babin et al. | |
| 5,449,653 A | 9/1995 | Briggs et al. | |
| 5,506,273 A | 4/1996 | Haruta et al. | |
| 5,717,126 A * | 2/1998 | Paciello et al. | 558/78 |
| 5,731,472 A | 3/1998 | Leung et al. | |
| 5,741,945 A | 4/1998 | Bryant et al. | |
| 5,763,679 A | 6/1998 | Nicholson et al. | |
| 5,874,639 A | 2/1999 | Nicholson et al. | |
| 5,874,640 A | 2/1999 | Bryant et al. | |
| 5,874,641 A | 2/1999 | Burke et al. | |
| 5,892,119 A | 4/1999 | Bryant et al. | |
| 5,910,600 A | 6/1999 | Urata et al. | |
| 5,929,289 A | 7/1999 | Abatjoglou et al. | |
| 5,932,772 A | 8/1999 | Argyropoulos et al. | |
| 5,952,530 A | 9/1999 | Argyropoulos et al. | |
| 5,965,754 A | 10/1999 | Clark et al. | |

(Continued)

FOREIGN PATENT DOCUMENTS

| | | |
|---|---|---|
| CN | 1857776 | 11/2006 |
| CN | 1986055 | 6/2007 |
| FR | 2717480 | 9/1995 |
| JP | 2006143653 | 6/2006 |
| KR | 1020060118369 | 11/2006 |
| WO | WO 2010117391 A1 * | 10/2010 |

OTHER PUBLICATIONS

PCT Written Opinion of the International Searching Authority (Apr. 9, 2013).*

Matsumoto, Mitsuo; Tamura, Masuhiko, "Rhodium-Catalyzed Low Pressure Hydroformylation of Substituted Terminal Olefins. Role of Bis(diphenylphosphino)alkane in Combination with Excess Triphenylphosphine", Journal of Molecular Catalysis (1982), 16, 195-207.

(Continued)

*Primary Examiner* — Porfirio Nazario Gonzalez
(74) *Attorney, Agent, or Firm* — Paul D. Hayhurst

(57) ABSTRACT

A combination of calixarene bisphosphite ligand and an organophosphine ligand. The combination can be employed with a catalytic metal to form a complex catalyst. The catalyst can be employed in ahydroforaiylation process for producing a mixture of aldehydes.

14 Claims, No Drawings

(56) References Cited

U.S. PATENT DOCUMENTS

| | | | |
|---|---|---|---|
| 6,031,116 A | 2/2000 | Bowman et al. | |
| 6,090,987 A | 7/2000 | Billig et al. | |
| 6,153,800 A | 11/2000 | Gelling et al. | |
| 6,255,499 B1 | 7/2001 | Kuperman et al. | |
| 6,294,700 B1 | 9/2001 | Kanel et al. | |
| 6,303,829 B1 | 10/2001 | Kanel et al. | |
| 6,303,830 B1 | 10/2001 | Argyropoulos et al. | |
| 6,307,109 B1 | 10/2001 | Kanel et al. | |
| 6,307,110 B1 | 10/2001 | Argyropoulos et al. | |
| 6,831,035 B2 | 12/2004 | Puckette et al. | |
| 6,906,225 B2 | 6/2005 | Puckette et al. | |
| 7,173,138 B2 | 2/2007 | Ahlers et al. | |
| 7,446,231 B2 | 11/2008 | Peterson et al. | |
| 7,863,487 B2 | 1/2011 | Eisenschmid et al. | |
| 7,906,688 B2 * | 3/2011 | Brammer et al. | 568/454 |
| 8,053,605 B2 | 11/2011 | Choi et al. | |
| 8,507,731 B2 * | 8/2013 | Brammer | 568/454 |
| 8,513,469 B2 | 8/2013 | Brammer | |
| 2006/0224000 A1 | 10/2006 | Papp et al. | |
| 2007/0112220 A1 | 5/2007 | Caers et al. | |
| 2007/0123735 A1 * | 5/2007 | Jeon et al. | 568/455 |
| 2008/0281128 A1 | 11/2008 | Karvinen et al. | |
| 2011/0207903 A1 | 8/2011 | Fontaine et al. | |

OTHER PUBLICATIONS

Matsumoto, Mitsuo; Tamura, Masuhiko, "Reinvestigation of Atmospheric Hydroformylation of 1-Octene Catalyzed by a Rhodium Complex. Some Advantages Given by Added Bis(diphenylphosphino)alkane", Journal of Molecular Catalysis (1982), 16, 209-216.

Hughes, O. Richard, et al., "Hydroformylation Catalyzed by Rhodium Complexes with Diphosphine Ligands", Journal of Molecular Catalysis, 1981, 12, 71-83.

Semeril David, et al., "Highly Regioselective Hydroformylation with Hemispherical Chelators", Chemistry—A European Journal, vol. 14, 2008, pp. 7144-7155.

Kunze, Christine, et al., "Calix[4]arene-based Bis-phosphonites, Bis-phosphites, and Bis-O-acyl-phosphites as Ligands in the Rhodium(I)-catalyzed Hydroformylation of 1-Octene", Z. Anorg. Allg. Chem., 2002, 628, 779-787.

Billig et al., "Oxo Process", Kirk-Othmer, Encyclopedia of Chemical Technology, 4th Edition, 1996, p. 1-17.

Steyer et al., "Bis-phosphites and bis-phosphinites based on distally-functionalised calix[4]arenes: coordination chemistry and use in rhodium-catalysed, low-pressure olefin hydroformylation", Dalton Transactions, 2005, 1301-1309.

Cobley et al., Rhodium(I) complexes of robust phosphites derived from calix(4)arenes and their application in the hydroformylation of 1-hexene., J. Chem. Soc., Dalton Trans., 2000, 628, 1109-1112.

Yasuhiro et al., "Production of Aldehydes", Patent abstract of JP11-255696, Sep. 21, 1999.

Yasuhiro et al., "Production of Aldehydes", Patent abstract of JP11-246464, Sep. 14, 1999.

"Oxo Alcohols", Process Economic Program Report 21D, Dec. 1999, p. 4.24-4.36.

* cited by examiner

HYDROFORMYLATION PROCESS

CROSS-REFERENCE TO RELATED APPLICATIONS

This application claims priority from U.S. provisional application Ser. No. 61/389,972, filed Oct. 5, 2010, which is incorporated herein by reference in its entirety.

BACKGROUND OF THE INVENTION

This invention pertains to an improved process for hydroformylating an olefinically-unsaturated compound to produce a mixture of aldehyde products.

It is well known in the art that one or more aldehyde products can be produced by contacting an olefin with carbon monoxide and hydrogen under reaction conditions in the presence of a metal-organophosphorus ligand complex catalyst. One such process, as exemplified in U.S. Pat. Nos. 4,148,830, 4,717,775, and 4,769,498, involves continuous hydroformylation with recycle of a solution containing the metal-organophosphorus ligand complex catalyst, with rhodium being an example of a suitable metal. The mixture produced typically includes linear, or normal, and branched aldehyde products. In some economic conditions, a high normal to branched (normal/branched or N/I) isomer ratio of the product aldehydes is desired.

The N/I ratio of a rhodium-catalyzed hydroformylation is determined primarily by the ligand employed. Because it is inexpensive, and gives rise to a relatively active and selective catalyst, triphenylphosphine (TPP) is often used for industrial hydroformylation processes. Although the rhodium/TPP catalyst is successfully practiced in facilities worldwide, it is limited to about a 10:1 ratio of normal to iso-aldehyde product. Normal aldehydes often have a higher value in the marketplace, thus it would be desirable for those currently operating rhodium/TPP-based processes to be able to increase their production of normal aldehyde in a facile, cost-effective manner.

In a rhodium/TPP system, the number of TPP molecules coordinated to rhodium is proportional to the concentration of TPP employed. At low concentration (e.g. 5-10 moles TPP per mole of rhodium), most rhodium complexes will contain only one TPP molecule. Such complexes are quite active, but generate a low N/I product. Because the selectivity of a rhodium/TPP catalyst increases as the concentration of TPP increases, commercial rhodium/TPP systems are typically operated with a large excess of TPP (e.g. 100-200 moles per mole of rhodium).

WO 2009/035204 teaches increasing the N/I produced by a rhodium/TPP hydroformylation catalyst via the addition of an additional phosphine ligand and a phosphine oxide. However, WO 2009/035204 only demonstrates the enhancement for TPP levels of 50 to 60 moles per mole of rhodium. Because it is well known that the concentration of TPP directly affects the nature of the TPP/rhodium complex, the skilled person would anticipate that a catalyst system containing commercial levels of TPP (100-200 moles TPP per mole of rhodium) would behave quite differently than one containing only 60 moles of TPP. Moreover a simpler process where one could increase the N/I by adding a single additional component would be desirable.

Bisphosphites are known to be active and selective ligands for rhodium hydroformylation. However, EP 0839787 indicates that a rhodium/bisphosphite complex would be vulnerable to additional coordination by TPP. This would result in low-activity, tri-phosphorous complexes. Therefore, the skilled person would expect that bisphosphites would not be capable of increasing the N/I of a rhodium/TPP catalyst employing commercial levels of TPP ligand without a critical loss of reaction rate.

SUMMARY OF THE INVENTION

The invention in one aspect is a composition comprising a calixarene bisphosphite ligand and an organophosphine ligand. In one embodiment, the invention is a catalytic complex comprising a transition metal complexed with a calixarene bisphosphite ligand and an organophosphine ligand. The invention further includes a process comprising contacting CO, $H_2$ and at least one olefin under hydroformylation conditions sufficient to form at least one aldehyde product in the presence of a catalyst having as components a transition metal, a calixarene bisphosphite ligand and an organophosphine ligand.

Surprisingly, a combination of a calixarene bisphosphite ligand and an organophosphine ligand can be employed to reversibly obtain higher N/I ratios, compared to the organophosphine alone, with a commercially acceptable reaction rate.

Aldehydes produced by hydroformylation have a wide range of utility including, for example, as intermediates for hydrogenation to aliphatic alcohols, for amination to aliphatic amines, for oxidation to aliphatic acids, and for aldol condensation to produce plasticizers.

DETAILED DESCRIPTION OF THE INVENTION

The invention described herein provides for a composition comprising a calixarene bisphosphite ligand and an organophosphine ligand. In one embodiment, the invention is a catalytic complex comprising a transition metal complexed with a calixarene bisphosphite ligand and an organophosphine ligand. The invention further includes a process comprising contacting CO, $H_2$ and at least one olefin under hydroformylation conditions sufficient to form at least one aldehyde product in the presence of a catalyst having as components a transition metal, a calixarene bisphosphite ligand and an organophosphine ligand.

Syngas (from synthesis gas) is the name given to a gas mixture that contains varying amounts of carbon monoxide (CO) and hydrogen ($H_2$). Production methods are well known and include, for example: (1) steam reforming and partial oxidation of natural gas or liquid hydrocarbons; and (2) the gasification of coal and/or biomass. Hydrogen and CO typically are the main components of syngas, but syngas may contain carbon dioxide and inert gases such as $N_2$ and Ar. The ratio of $H_2$ to CO varies greatly but generally ranges from 1:100 to 100:1 and preferably is between 1:10 and 10:1. Syngas is commercially available and is often used as a fuel source or as an intermediate for the production of other chemicals. The most preferred $H_2$:CO ratio for chemical production is between 3:1 and 1:3 and the ratio usually is targeted to be between about 1:2 and 2:1 for most hydroformylation applications.

The olefinic compound employable in the hydroformylation process of this invention can be substituted or unsubstituted and includes both optically active (prochiral and chiral) and non-optically active (achiral) unsaturated compounds containing from 2 to 40, preferably 3 to 20, carbon atoms and one or more carbon-carbon double bonds (C=C). Such olefinic compounds can be terminally or internally unsaturated and be of straight-chain, branched chain, or cyclic structures. Olefin mixtures, such as obtained from the oligomerization of propene, butene, and isobutene, (such as, so called dimeric, trimeric or tetrameric propylene, as disclosed, for example, in U.S. Pat. Nos. 4,518,809 and 4,528,403, incorporated herein by reference) may also be employed, as well as mixed butenes, for example, raffinate I and raffinate II known to the skilled person. Such olefinic compounds and the corresponding aldehyde products derived therefrom may also contain one or more groups or substituents that do not adversely affect the hydroformylation process of this invention; suitable groups or substituents being described, for example, in U.S. Pat. Nos. 3,527,809, and 4,769,498, incorporated herein by reference.

Most preferably, the subject invention is especially useful for the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, for example, methyl pentenoate; alkenyl alkanoates, alkenyl alkyl ethers, alkenols, for example, pentenols; alkenals, for example, pentenals; such species to include allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, oleic acid and esters thereof, such as methyl oleate, and homologous unsaturated fatty acids and unsaturated fatty acid esters. Many olefinic compounds are commercially available.

Two different organophosphorus ligands are employed in the hydroformylation process, namely a calixarene bisphosphite ligand and an organophosphine ligand, both of which are capable of bonding to a transition metal to form a transition metal-organophosphorus ligand complex catalyst capable of catalyzing the hydroformylation process.

Suitable metals that can be employed as the metal in the transition metal-ligand complex catalyst include Group VIII metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, and most preferably, rhodium. Other permissible metals include Group VIB metals selected from chromium (Cr), molybdenum (Mo), tungsten (W), and mixtures thereof. Mixtures of metals from Groups VIB and VIII may also be used in this invention.

The metal is employed in a catalytic amount. In one embodiment, the amount of metal employed is at least about 1 ppm, based on the weight of the reaction fluid in the reaction vessel. Advantageously, the amount of metal employed is from about 1 ppm to about 1000. The amount of metal employed can also be from about 20 ppm to about 500 ppm, or from about 100 ppm to about 300 ppm.

The calixarene bisphosphite ligand comprises two phosphorus (III) atoms each bonded to three hydrocarbyloxy radicals, any non-bridging species of which consists essentially of a substituted or unsubstituted aryloxy radical. In this invention, the calixarene bisphosphite ligand is represented by the following formula:

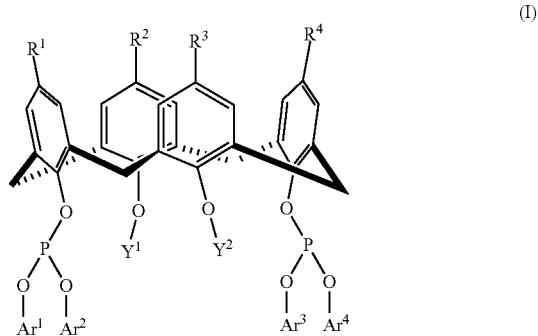

(I)

wherein the calixarene is a calix[4]arene; each $R^1$, $R^2$, $R^3$, and $R^4$ is independently selected from the group consisting of hydrogen and substituted or unsubstituted alkyl radicals; each $Y^1$ and $Y^2$ is independently selected from the group consisting of substituted and unsubstituted monovalent alkyl, alkaryl, aralkyl, and amide radicals; and wherein each $Ar^1$, $Ar^2$, $Ar^3$, and $Ar^4$ is independently selected from substituted and unsubstituted monovalent aryl radicals, or alternatively, wherein $Ar^1$ and $Ar^2$ are connected to form a substituted or unsubstituted divalent arylene radical and/or $Ar^3$ and $Ar^4$ are connected to form a substituted or unsubstituted divalent arylene radical. In one embodiment, each $R^1$, $R^2$, $R^3$, and $R^4$ is independently t-butyl. In one embodiment, each $Y^1$ and $Y^2$ is independently N, N' diethyl amido.

A preferred calixarene bisphosphite composition is represented by the following formula:

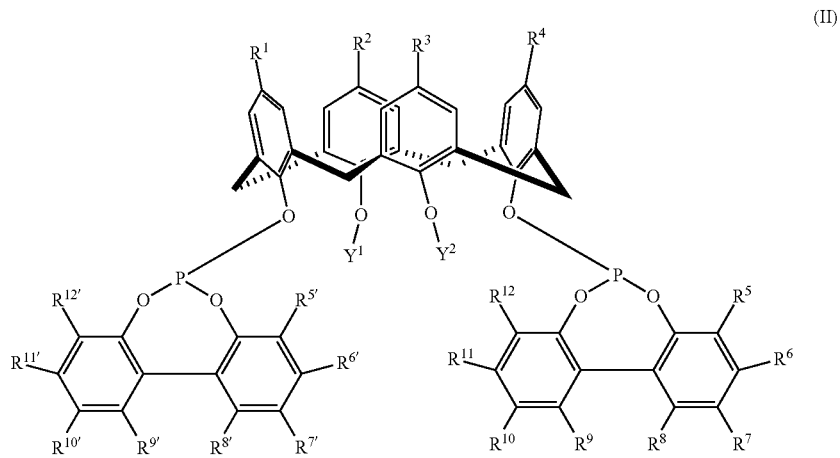

(II)

wherein the calixarene is a calix[4]arene; each $R^1$, $R^2$, $R^3$, and $R^4$ is independently selected from the group consisting of hydrogen and substituted or unsubstituted monovalent alkyl radicals; each $Y^1$ and $Y^2$ is independently selected from the group consisting of substituted and unsubstituted monovalent alkyl, alkaryl, aralkyl, and amide radicals; and each $R^5$, $R^6$, $R^7$, $R^8$, $R^9$, $R^{10}$, $R^{11}$, $R^{12}$, $R^{5'}$, $R^{6'}$, $R^{7'}$, $R^{8'}$, $R^{9'}$, $R^{10'}$, $R^{11'}$, and $R^{12'}$, is independently selected from hydrogen, alkyl, alkaryl, alkoxy, aryloxy, keto, carbonyloxy, and alkoxycarbonyl groups.

In a most preferred embodiment, the calixarene bisphosphite ligand comprises N,N-diethylacetamide-p-tert-butylcalix[4]arene bisphosphite which is represented by the following formula (IIa):

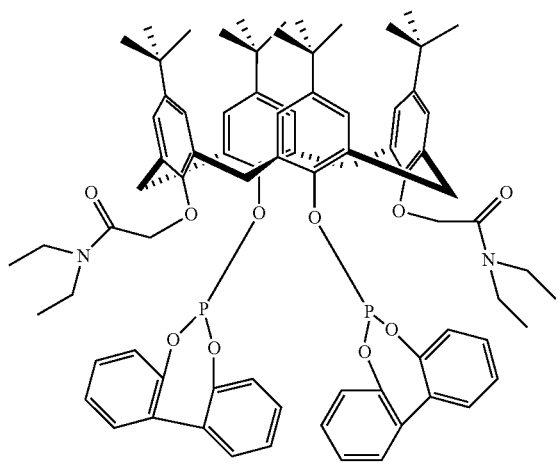

(IIa)

The calixarene bisphosphite ligand of formula IIa can be prepared as described in US Patent Application Publication 2010/0044628. Similar techniques can be used to prepare the ligands of formulas I and II, as known to those skilled in the art. Combinations of calixarene bisphosphite ligands can be employed as the calixarene bisphosphite ligand.

In a preferred embodiment, the organophosphine ligand is a triarylphosphine represented by the following formula:

P(R)$_3$ wherein each R is the same or different and is a substituted or unsubstituted aryl radical. Examples of organophosphine ligands include tribenzylphosphine, triphenylphosphine, tri-o-tolylphosphine, tri-m-tolylphosphine, tri-p-tolylphosphine, tris(o-methoxyphenyl)phosphine, tris(m-methoxyphenyl)phosphine, tris(p-methoxyphenyl)phosphine, tris(p-trifluoromethylphenyl)phosphine, tris(2,4,6,-trimethoxyphenyl)phosphine, tris(pentafluorophenyl)phosphine, tris(p-fluorophenyl)phosphine, tris(3,5-dimethylphenyl)phosphine, tri(mesityl)phosphine, cyclohexyldiphenylphosphine, benzyldiphenylphosphine, dicyclohexylphenylphosphinetribenzylphosphine, tricyclohexyphosphine. Triphenylphosphine is preferred in view of its low cost and ready availability.

The amount of organophosphine ligand employed is an amount that is sufficient to form a catalytic complex. A wide range of organophosphine ligand concentrations can be employed. As known to those skilled in the art, the concentration of organophosphine ligand employed has a known impact on hydroformylation process, including the product mix and reaction rate. For example, in various embodiments, the molar ratio of organophosphine ligand to catalytic metal can be from about 10 (i.e. 10:1) to about 300, from about 100 to about 250, and from about 150 to about 200. In one embodiment, the molar ratio of organophosphine to catalytic metal is at least 150:1, and can be greater than 150:1.

In a preferred embodiment, the organophosphine ligand is a triarylphosphine. In a more preferred embodiment, the organophosphine ligand is triphenylphosphine. Combinations of organophosphine ligands can be employed as the organophosphine ligand. Many of the organophosphine ligands are commercially available, and others can be synthesized using known organic chemistry synthetic techniques.

It is to be noted that the successful practice of this hydroformylation process invention does not depend and is not predicated upon the exact formula of the catalytically active metal complex species, which may be present in a mononuclear, dinuclear, or higher nuclearity form. Indeed, the exact formula of the catalytically active metal ligand complex may be difficult to determine analytically. Although not intended to be bound to any theory or mechanistic discourse, it appears that the active catalytic species in its general form comprises various combinations of the transition metal in complex combination with one or more ligands. For example, the active catalytic species may comprise one or more organophosphine ligands and/or one or more calixarene bisphosphite ligands, further in combination with carbon monoxide. The catalytically active composition may also contain one or more additional ligands, such as hydrogen, or an anion satisfying the coordination sites or nuclear charge of the transition metal. Illustrative additional ligands include halogen (Cl$^-$, Br$^-$, F), alkyl, aryl, substituted aryl, $CF_3^-$, $C_2F_5^-$, $CN^-$, $R'_2PO^-$, $R'P(O)(OH)O^-$ (wherein each R' is independently alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2{=}CHCH_2^-$, $C_6H_5CN$, $CH_3CH{=}$, NO, $NH_3$, pyridine, $(C_2H_5)_3N$, mono-olefins, diolefins, triolefins, and tetrahydrofuran.

The transition metal-ligand complex catalyst can be prepared by methods known in the art. In one instance, the catalyst may be preformed and introduced into the reaction medium of a hydroformylation process. Standard identification methods may be used to identify the complex catalyst or catalyst precursor composition and its ligand components, including for example, elemental analysis, mass spectroscopy, infrared spectroscopy, and $^1$H, $^{31}$P, and/or $^{13}$C NMR spectroscopy, as known to the skilled person and mentioned hereinbelow.

Preferably, the transition metal-ligand complex catalyst of this invention is derived from a transition metal source material that is introduced into the hydroformylation reaction medium to provide for in situ formation of the active catalyst. Preferred are Group VIII metal source materials; for example, rhodium source materials, such as, rhodium acetylacetonate, rhodium dicarbonyl acetylacetonate, $Rh_2O_3$, $Rh_4(CO)_{12}$, [$RhCl(CO)_2$]$_2$, $Rh_6(CO)_{16}$, $Rh(NO_3)_3$, and the like may be introduced into the hydroformylation reaction medium along with the ligand or ligands for the in situ formation of the active catalyst. In one embodiment, the calixarene bisphosphite ligand can be added to a system wherein a transition metal-organophosphine ligand is already present. For example, a reaction system can be started up with only a transition metal-organophosphine ligand, and a calixarene bisphosphite ligand can be added to it. In one embodiment, rhodium dicarbonyl acetylacetonate is employed as a rhodium source and reacted in the presence of a solvent with the calixarene bisphosphite ligand to form a catalytic rhodium-calixarene bisphosphite ligand complex precursor composition, which is introduced into the reactor along with excess free calixarene bisphosphite ligand for the in situ formation of the active catalyst. The reaction conditions sufficient for formation of the complex catalyst or catalyst precursor in most cases will be similar to the hydroformylation reaction conditions described hereinbelow.

The term "complex" as used herein means a coordination compound formed by the union of one or more electronically rich molecules or atoms (i.e., ligand) with one or more electronically poor molecules or atoms (i.e., transition metal). For example, the organophosphine ligand employable herein possesses one phosphorus (III) donor atom having one unshared pair of electrons, which is capable of forming a coordinate covalent bond with the metal. The calixarene bisphosphite ligand employable herein possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand(s) such as described above, for example, hydrogen, mono-olefin, or an anion satisfying the coordination sites or nuclear charge of the metal.

The number of available coordination sites on the transition metal is well known in the art and depends upon the particular transition metal selected. The catalytic species may comprise a complex catalyst mixture of monomeric, dimeric or higher nuclearity forms, which forms preferably are characterized by at least one organophosphorus-containing molecule complexed per one molecule of metal, for example, rhodium. For instance, it is considered that the catalytic species of the preferred catalyst employed in the hydroformylation reaction may be complexed with carbon monoxide and hydrogen in addition to either the calixarene bisphosphite ligand or the organophosphine ligand.

As used hereinafter, the term "reaction fluid" or "reaction product fluid" is contemplated to include, but not limited to, a reaction mixture comprising: (a) a calixarene bisphosphite ligand; (b) an organophosphine ligand (c) a transition metal-ligand complex catalyst wherein the ligand is selected from a mixture in the fluid of the ligands described above, including at a minimum the calixarene bisphosphite ligand and the organophosphine ligand, (d) two or more aldehyde products formed in the reaction, (e) optionally, unconverted reactants including unreacted olefin, and (f) an organic solubilizing agent for said metal-ligand complex catalyst and said free ligand. It is to be understood that the hydroformylation reaction fluid may contain minor amounts of additional ingredients, such as those that have either been deliberately added or formed in situ during the process. Examples of such additional ingredients include carbon monoxide and hydrogen gases, and in situ formed products, such as saturated hydrocarbons, and/or unreacted isomerized olefins corresponding to the olefin starting materials, and/or high boiling liquid aldehyde condensation byproducts, and/or one or more degradation products of the catalyst and/or organophosphorus ligands, including by-products formed by hydrolysis of the organophosphorus ligands, as well as inert co-solvents or hydrocarbon additives, if employed.

In one embodiment, the molar ratio of calixarene bisphosphite ligand to catalytic metal is from about 0.2 to about 15. In another embodiment, the ratio of calixarene bisphosphite ligand to organophosphine ligand is from about 0.8 to about 10. In yet another embodiment, the ratio of calixarene bisphosphite ligand to organophosphine ligand is from about 1 to about 5.

In one embodiment, the invention is a hydroformylation process for producing a mixture of aldehydes, the process comprising contacting under continuous reaction conditions in a hydroformylation reaction fluid, one or more olefinically-unsaturated compounds, carbon monoxide, and hydrogen in the presence of a mixture of a calixarene bisphosphite ligand and an organophosphine ligand, at least one of said ligands being bonded to a transition metal to form a transition metal-ligand complex hydroformylation catalyst, such that a mixture of aldehydes is produced.

The hydroformylation processing techniques applicable to this invention may correspond to any of the processing techniques known and described in the art. Preferred processes are those involving catalyst liquid recycle hydroformylation processes, as described in U.S. Pat. Nos. 4,668,651; 4,774,361; 5,102,505; 5,110,990; 5,288,918; 5,874,639; 6,090,987; and extractive hydroformylation processes, as described in U.S. Pat. Nos. 5,932,772; 5,952,530; 6,294,700; 6,303,829; 6,303,830; 6,307,109; and 6,307,110; the disclosures of which are incorporated herein by reference.

Generally, such catalyzed liquid hydroformylation processes involve production of aldehydes by contacting an olefinic unsaturated compound with carbon monoxide and hydrogen in the presence of a transition metal-organophosphorus ligand complex catalyst in a liquid phase that may also contain an organic solvent for the catalyst and ligand. Free organophosphorus ligand is also present in the liquid phase. In this invention, the generic term "organophosphorus ligand" embraces both types of ligands: calixarene bisphosphite and organophosphine. Both ligands are required; but no inference is made that both ligands are always complexed to the transition metal. Rather, the ligands may be complexed or unbound as catalytic cycling and competition between ligands for transition metal may dictate. By "free organophosphorus ligand" is meant an organophosphorus ligand that is not complexed with (tied to or bound to) the metal, for example, rhodium atom, of the complex catalyst. Generally, the hydroformylation process may include a recycle method, wherein a portion of the liquid reaction fluid containing the catalyst and aldehyde product is withdrawn from the hydroformylation reactor (which may include one reaction zone or a plurality of reaction zones, for example, in series), either continuously or intermittently; and the aldehyde product is separated and recovered therefrom by techniques described in the art; and then a metal catalyst-containing residue from the separation is recycled to the reaction zone as disclosed, for example, in U.S. Pat. No. 5,288,918. If a plurality of reaction zones is employed in series, the reactant olefin may be fed to the first reaction zone only; while the catalyst solution, carbon monoxide, and hydrogen may be fed to each of the reaction zones.

In one embodiment of the claimed process, the N/I isomer ratio may vary continuously within a range from about 1/1 to about 100/1, depending upon the olefin substrate and the particular ligand pair selected. More preferably, the N/I isomer ratio can vary from greater than about 13/1 to less than about 75/1, more preferably, less than about 50/1.

In another preferred embodiment of this invention, when the concentration of calixarene bisphosphite ligand is increased, the N/I isomer ratio of aldehyde products increases; and when the concentration of calixarene bisphosphite ligand is decreased, the N/I isomer ratio of aldehyde products decreases.

The hydroformylation process of this invention may be asymmetric or non-asymmetric, the preferred process being non-asymmetric, and is conducted in any continuous or semi-continuous fashion; and may involve any conventional catalyst-containing hydroformylation reaction fluid and/or gas and/or extraction recycle operation, as desired. As used herein, the term "hydroformylation" is contemplated to include all operable asymmetric and non-asymmetric processes that involve converting one or more substituted or unsubstituted olefinic compounds or a reaction mixture comprising one or more substituted or unsubstituted olefinic compounds, in the presence of carbon monoxide, hydrogen, and a hydroformylation catalyst, to a product comprising a mixture of substituted or unsubstituted aldehydes.

In this invention, the N/I isomer ratio of a hydroformylation process that employs a transition metal/organophosphine catalyst may be increased by adding a calixarene bisphosphite ligand. Moreover the N/I isomer ratio may be increased based on the amount of calixarene bisphosphite ligand added relative to the transition metal. Without being bound by theory, it is thought that the thermodynamic stability which results from the formation of the transition metal/calixarene bisphosphite chelate ring ensures that the calixarene bisphosphite will preferentially complex the transition metal relative to the organophosphine. This chelate effect holds sway even though the concentration of the organophosphine in the catalyst solution is significantly higher. Moreover it is thought that the steric bulk of the resulting transition metal/calixarene bisphosphite complex is sufficient to hinder the organophosphine from approaching the transition metal center, and thus forming low activity, transition metal/triphosphorous species.

The concentrations of transition metal, calixarene bisphosphite ligand, and organophosphine ligand in the hydroformylation reaction fluid can be readily determined by well known analytical methods. From these concentration analyses, the required molar ratios can be readily calculated and tracked. The transition metal, preferably rhodium, is best determined by atomic absorption or inductively coupled plasma (ICP) techniques. The ligands are best quantized by $^{31}P$ nuclear magnetic resonance spectroscopy (NMR) or by high pressure liquid phase chromatography (HPLC) of aliquots of the reaction fluid. On-line HPLC can also be used to monitor the concentrations of the ligands and the transition metal-ligand complexes. The different ligands should be characterized separately (e.g., without the presence of transition metal in the reaction fluid) in a quantitative manner to establish chemical shifts and/or retention times using appropriate internal standards as needed. The transition metal-calixarene bisphosphite ligand and transition metal-organophosphine ligand complexes can be observed via any of the above-identified analytical methods to enable quantification of the complexed ligand(s).

The concentration of calixarene bisphosphite ligand in the hydroformylation reaction fluid can be increased in any suitable manner, for example, by adding a quantity of calixarene bisphosphite ligand in one batch or in incremental additions to the hydroformylation reactor, or by continuously or intermittently adding a quantity of calixarene bisphosphite ligand to a liquid feed to the reactor comprising solubilizing agent (solvent), catalyst, organophosphine ligand, and optionally liquid olefinic compound. Alternatively, calixarene bisphosphite ligand can be added into a recycle stream (or a unit that produces a recycle stream) at any point downstream of the hydroformylation reactor for cycling back to said reactor. For example, calixarene bisphosphite ligand can be added to an extractor that processes the hydroformylation product fluid to recover a recycle stream containing the organophosphine, the original and additional quantities of calixarene bisphosphite, and a solubilizing agent, which are cycled back to the hydroformylation reactor. Likewise, the concentration of calixarene bisphosphite ligand in the hydroformylation reaction fluid can be decreased in any suitable manner; for example, the concentration of calixarene bisphosphite ligand can be decreased over time through hydrolytic attrition resulting from reaction of the ligand with quantities of water present in the reaction fluid. Alternatively, a suitable quantity of oxidant, such as oxygen, air, hydrogen peroxide, organic hydroperoxides, more specifically, alkyl hydroperoxides, such as tertiary-butyl hydroperoxide, or aryl hydroperoxides, such as ethylbenzene hydroperoxide or cumene hydroperoxide, can be deliberately added to the hydroformylation reaction fluid to accelerate destructive oxidation of the calixarene bisphosphite ligand. At any time during the continuous hydroformylation process, additional calixarene bisphosphite and/or organophosphine ligand(s) can be supplied to the reaction fluid to make-up for such ligand lost through degradation. Other methods may be employed to lower the concentration of calixarene bisphosphite ligand relative to transition metal. For example, downstream extraction or vaporization of the hydroformylation product stream may be conducted under process conditions (e.g., pH or elevated temperature) selected to degrade a portion of the calixarene bisphosphite ligand so as to reduce its concentration in a recycle stream returning to the hydroformylation reactor. The skilled process engineer may envision other means and methods of raising or lowering the calixarene bisphosphite concentration relative to transition metal.

In this invention, in general, increasing the molar ratio of calixarene bisphosphite ligand to transition metal increases the N/I isomer ratio in the aldehyde product. In practice, the observed N/I isomer ratio of the aldehyde product indicates whether to add calixarene bisphosphite ligand (typically to increase the N/I ratio) or to add water or oxidant (typically to lower the N/I ratio). The degree to which one chooses to raise or lower the isomer ratio is governed by the selected target N/I isomer ratio (e.g., as determined by market demands). For a small degree of deviation (<+/−1) from the target N/I ratio, a preferred practice is to add unit portions of the calixarene bisphosphite ligand or water or oxidant to the reactor intermittently until the target N/I ratio is reached. A "unit portion" consists of a molar charge of calixarene bisphosphite ligand or water or oxidant taken as about 5 to about 10 mole percent of the initial moles of calixarene bisphosphite charged to the reactor. For a large degree of deviation (>+/−1) from the target N/I ratio, several unit portions can be combined into larger portions that are added to the reactor. In continuous operation, a continuous or intermittent addition of the unit portion(s) of calixarene bisphosphite ligand or water or oxidant can be made directly into the reactant feed to the reactor or via a separate feed line. In continuous operations, one may choose to time the additions of the calixarene bisphosphite ligand based on prior experience with the rate of decay of said ligand to achieve stable calixarene bisphosphite ligand concentration with a resulting desired and stable N/I isomer ratio. The N/I isomer ratio is readily determined by gas chromatography (GC) analysis of the product stream from the reactor either from the vapor space (e.g., a vent stream) or liquid sample of the product fluid taken directly from the reactor or from a downstream product-catalyst separation stage (e.g., vaporizer).

In this invention, control over the N/I isomer ratio is usually smooth and continuous rather than discontinuous or abrupt, such as, a "step-ladder" increase or decrease.

In general, the hydroformylation process of this invention can be conducted at any operable reaction temperature. Preferably, the reaction temperature is greater than about −25° C., more preferably, greater than about 50° C. Preferably, the reaction temperature is less than about 200° C., preferably, less than about 120° C.

Generally, the total gas pressure comprising carbon monoxide, hydrogen, and olefinic reactant(s) may range from about 1 psia (6.9 kPa) to about 10,000 psia (69,000 MPa). In general, however, it is preferred that the process be operated at a total gas pressure comprising carbon monoxide, hydrogen, and olefin reactant(s) of greater than about 25 psia (172 kPa) and less than about 2,000 psia (14,000 kPa) and more preferably less than about 500 psia (3500 kPa). More specifically the carbon monoxide partial pressure of the hydroformylation process of this invention may vary from about 10 psia (69 kPa) to about 1,000 psia (6,900 kPa), and more preferably from about 10 psia (69 kPa) to about 800 psia (5,500 kPa), and even more preferably, from about 15 psia (103.4 kPa) to about 200 psia (1378 kPa); while the hydrogen partial pressure ranges preferably from about 5 psia (34.5 kPa) to about 500 psia (3,500 kPa), and more preferably from about 10 psia (69 kPa) to about 300 psia (2,100 kPa).

The syngas feed flow rate may be any operable flow rate sufficient to obtain the desired hydroformylation process. Typically, the syngas feed flow rate can vary widely depending upon the specific form of catalyst, olefin feed flow rate, and other operating conditions. Suitable syngas feed flow rates and vent flow rates are described in the following reference: "Process Economics Program Report 21D: Oxo Alcohols 21d," SRI Consulting, Menlo Park, Calif., Published December 1999, incorporated herein by reference.

In one embodiment, the reaction rate is at least 0.2 g-mol/l-hr. Preferably, the reaction rate is at least 1 g-mol/l-hr. The upper limit of reaction rate is governed by practical factors.

The invention will be further clarified by a consideration of the following examples, which are intended to be purely exemplary of the use of the invention. Other embodiments of the invention will be apparent to those skilled in the art from a consideration of this specification or practice of the invention as disclosed herein.

Specific Embodiments of the Invention

EXAMPLES 1-4

A rhodium catalyst precursor (dicarbonylacetylacetonato rhodium (I) (150 ppm rhodium), triphenylphosphine (TPP) (300 equivalents TPP/Rh, 10.3 wt %) and the N,N-diethylacetamide-p-tert-butylcalix [4] arene bisphosphite ligand (DE-Calix-BP, 0, 1, 2 and 3 equivalents/Rh) are weighed into a septum-capped bottle in a dry box. The solids are dissolved in toluene, and the resulting solution transferred via vacuum into a 100 ml Parr mini-reactor. The catalyst-containing solution is then preheated with agitation (1100 rpm) to 90° C. under 1:1 carbon monoxide:hydrogen (syngas) for 30 minutes. A pressure of 60 psig 1:1:1 gas (equal parts carbon monoxide:hydrogen:propylene) is established with a Brooks model 5866 flow meter, and held constant for a run time of 2 hours. Total gas uptake is measured with a Brooks 0151E totalizer. Liquid reaction samples are taken periodically and analyzed on an Agilent Technologies 6890 Gas Chromatograph (GC), equipped with a DB-1 30m×0.32 mm, 1μ film column. Component quantization is based on GC area percent exclusive of solvent. The results for a range of 0-3 equivalents per rhodium of DE-Calix-BP appear below:

| Example | DE/Calix-BP (L/Rh) | Initial Rate (g mol/l-hr) | Final N/I |
|---------|--------------------|---------------------------|-----------|
| 1*      | 0                  | 0.80                      | 6.0       |
| 2       | 1                  | 0.34                      | 8.0       |
| 3       | 2                  | 0.07                      | 16.3      |
| 4       | 3                  | 0.04                      | 18.5      |

*Not an embodiment of the invention

EXAMPLES 5-8

The procedure of examples 1-4 is repeated, except for the following changes to concentrations and conditions: 300 ppm rhodium, thus changing the concentration of TPP/Rh to 150 equivalents TPP/Rh, 4.7 g propylene added as a liquid, and 80 psig 1:1 carbon monoxide: hydrogen at 90° C. The results for a range of 0-3 equivalents per rhodium of DE-Calix-BP appear below:

| Example | DE/Calix-BP (L/Rh) | Initial Rate (g mol/l-hr) | Final N/I |
|---------|--------------------|---------------------------|-----------|
| 5*      | 0                  | 3.12                      | 3.4       |
| 6       | 1                  | 1.28                      | 5.5       |
| 7       | 2                  | 1.00                      | 10.4      |
| 8       | 3                  | 0.67                      | 13.3      |

*Not an embodiment of the invention

EXAMPLES 9-12

The procedure of examples 1-4 is repeated, except for the following changes to concentrations and conditions: 300 ppm rhodium, thus changing the concentration of TPP/Rh to 150 equivalents TPP/Rh, 5.5 g 1-butene added as a liquid, and 40 psig 1:1 carbon monoxide: hydrogen at 100° C. The results for a range of 0-3 equivalents per rhodium of DE-Calix-BP appear below:

| Example | DE/Calix-BP (L/Rh) | Initial Rate (g mol/l-hr) | Final N/I |
|---------|--------------------|---------------------------|-----------|
| 9*      | 0                  | 3.05                      | 6.0       |
| 10      | 1                  | 1.61                      | 9.1       |
| 11      | 2                  | 0.86                      | 16.3      |
| 12      | 3                  | 0.78                      | 24.5      |

*Not an embodiment of the invention

Comparative Experiments 13-16 (Not an Embodiment of the Invention)

The procedure of examples 9-12 is repeated, but instead of the calixarene bisphosphite ligand of the invention, Ligand B (pictured below) is used:

13

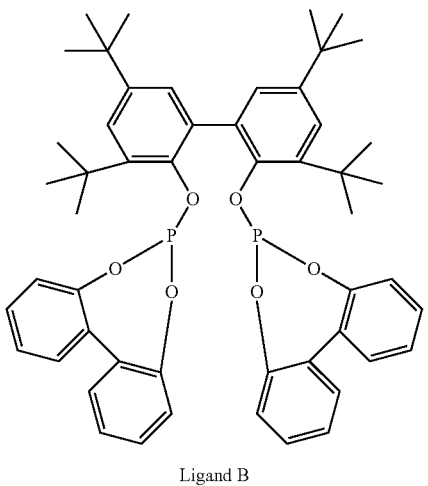 [SMILES: CC(C)(C)c1cc(-c2cc(C(C)(C)C)cc(C(C)(C)C)c2Op2oc3ccccc3c3ccccc3o2)c(Op2oc3ccccc3c3ccccc3o2)c(C(C)(C)C)c1]

Ligand B

The results for a range of 0-3 equivalents per rhodium of Ligand B appear below:

| Example | DE/Calix-BP (L/Rh) | Initial Rate (g mol/l-hr) | Final N/I |
|---------|--------------------|-----------------------------|-----------|
| 13*     | 0                  | 4.61                        | 6.0       |
| 14*     | 1                  | 2.04                        | 6.5       |
| 15*     | 2                  | 0.09                        | 81.5      |
| 16*     | 3                  | 0.08                        | 85.7      |

*Not an embodiment of the invention

Examples 2-4 surprisingly show that the N/I isomer ratio of a rhodium/triphenylphosphine catalyst can be increased by the addition of DE-Calix-BP. Moreover, Examples 6-8 demonstrate that the reaction rate of the rhodium/triphenylphosphine/DE-Calix-BP catalyst may be increased by employing more forcing reaction conditions. Examples 10-12 demonstrate the invention with an additional olefin (1-butene).

Comparative Experiments 13-16 clearly show that the surprising result of the invention is not readily duplicated by adding another bisphosphite ligand (Ligand B) to a rhodium/triphenylphosphine catalyst. The N/I ratio of Comparative Experiment 14 is not significantly different than that of Comparative Experiment 13. While the N/I ratio is very high for Comparative Experiments 15 and 16, the reaction rate is unacceptably low.

The invention claimed is:

1. A composition comprising a calixarene bisphosphite ligand and an organophosphine ligand.

2. The composition of claim 1 wherein the calixarene bisphosphite ligand is represented by the following formula:

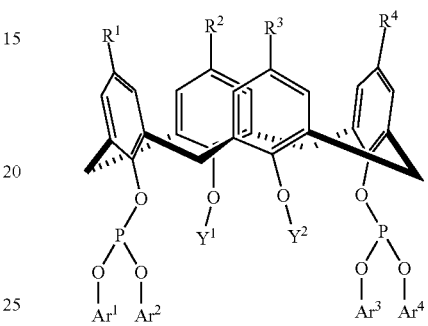

wherein the calixarene is a calix[4]arene; each $R^1$, $R^2$, $R^3$, and $R^4$ is independently selected from the group consisting of hydrogen and substituted or unsubstituted alkyl radicals; each $Y^1$ and $Y^2$ is independently selected from the group consisting of substituted and unsubstituted monovalent alkyl, alkaryl, aralkyl, and amide radicals; and wherein each $Ar^1$, $Ar^2$, $Ar^3$, and $Ar^4$ is independently selected from substituted and unsubstituted monovalent aryl radicals, or alternatively, wherein $Ar^1$ and $Ar^2$ are connected to form a substituted or unsubstituted divalent arylene radical and/or $Ar^3$ and $Ar^4$ are connected to form a substituted or unsubstituted divalent arylene radical.

3. The composition of claim 1 wherein the calixarene bisphosphite ligand is selected from the following formula:

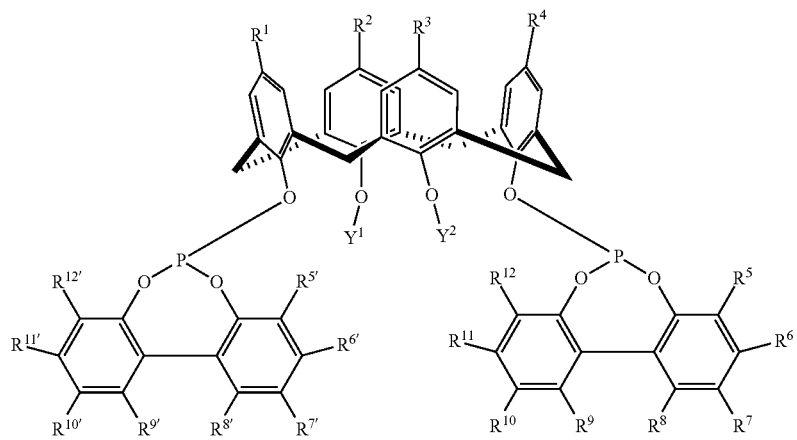

wherein the calixarene is a calix[4]arene; each $R^1$, $R^2$, $R^3$, and $R^4$ is independently selected from the group consisting of hydrogen and substituted or unsubstituted monovalent alkyl radicals; each $Y^1$ and $Y^2$ is independently selected from the group consisting of substituted and unsubstituted monovalent alkyl, alkaryl, aralkyl, and amide radicals; and each $R^5$, $R^6$, $R^7$, $R^8$, $R^9$, $R^{10}$, $R^{11}$, $R^{12}$, $R^{5'}$, $R^{6'}$, $R^{7'}$, $R^{8'}$, $R^{9'}$, $R^{10'}$, $R^{11'}$, and $R^{12'}$ is independently selected from hydrogen, alkyl, alkaryl, alkoxy, aryloxy, keto, carbonyloxy, and alkoxycarbonyl groups.

4. The composition of claim 1 wherein the calixarene bisphosphite ligand is:

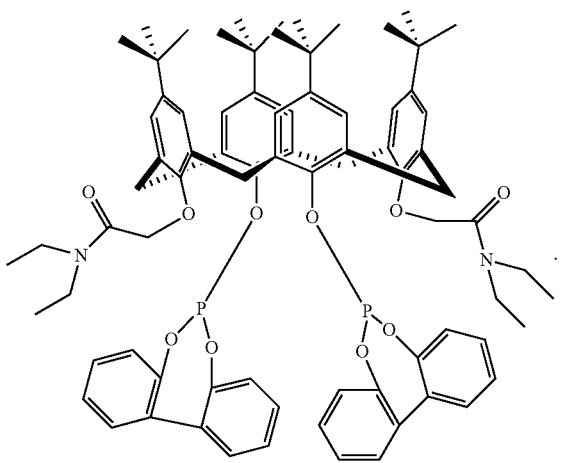

5. The composition of claim 1 wherein the organophosphine ligand is a triarylphosphine represented by the following formula:

$P(R)_3$ wherein each R is the same or different and is a substituted or unsubstituted aryl radical.

6. The composition of claim 1 wherein the organophosphine is triphenylphosphine.

7. A catalytic complex comprising a transition metal complexed with the ligands of a claim 1.

8. A process comprising contacting CO, $H_2$ and at least one olefin in the presence of a catalytic complex, the complex comprising a calixarene bisphosphite ligand and an organophosphine ligand of claim 1, under hydroformylation conditions sufficient to form at least one aldehyde product.

9. A process comprising contacting CO, $H_2$ and at least one olefin under hydroformylation conditions sufficient to form at least one aldehyde product in the presence of a catalyst having as components a transition metal, a calixarene bisphosphite ligand and an organophosphine ligand, wherein the molar ratio of organophosphine to catalytic metal is greater than 150:1, and the reaction rate is at least 0.2 g-mol/l-hr.

10. The process of claim 9 wherein the ratio of normal to branched products (the N/I ratio) is at least 13.

11. The process of claim 9 wherein the process is conducted in a reaction vessel, and the concentration of the transition metal is greater than about 1 part per million (ppm) and less than about 1,000 ppm, based on the weight of hydroformylation reaction fluid in the vessel.

12. The process of claim 9 wherein the process temperature is greater than about −25° C. and less than about 200° C., wherein the total gas pressure comprising carbon monoxide, hydrogen, and olefinic reactant(s) ranges from greater than about 25 psia (173 kPa) to less than about 2,000 psia (14,000 kPa), wherein the carbon monoxide partial pressure ranges from about 15 psia (103.4 kPa) to about 200 psia (1378 kPa), wherein the olefin is an achiral alpha-olefin having from 2 to 30 carbon atoms or an achiral internal olefin having from 4 to 20 carbon atoms, wherein carbon monoxide and hydrogen are present in quantities that provide an $H_2$:CO molar ratio ranging from 1:10 to 100:1, and wherein the transition metal is a Group VIII metal selected from rhodium, cobalt, iridium, ruthenium, and mixtures thereof.

13. The process of claim 9 wherein the olefin is propylene, the calixarene bisphosphite ligand is as described in claim 4, the organophosphine is triphenylphosphine, and the normal/branched aldehyde product isomer ratio ranges from 13/1 to 20/1.

14. The process of claim 9 wherein a mixture of calixarene bisphosphite ligands is employed; or wherein a mixture of organophosphine ligands is employed; or wherein together a mixture of calixarene bisphosphite ligands and a mixture of organophosphine ligands are employed.

* * * * *